US005858692A

United States Patent [19]
Friedman et al.

[11] Patent Number: 5,858,692
[45] Date of Patent: *Jan. 12, 1999

[54] POLYCHLORINATED BIPHENYLS (PCB) IMMUNOASSAY METHOD, ITS COMPONENTS AND A KIT FOR USE IN PERFORMING THE SAME

[75] Inventors: Stephen B. Friedman, Chapel Hill; William B. Studabaker, Durham; Randy L. Allen, Apex, all of N.C.

[73] Assignee: ENSYS, Inc., Research Triangle Park, N.C.

[ * ] Notice: The term of this patent shall not extend beyond the expiration date of Pat. No. 5,834,222.

[21] Appl. No.: 395,705

[22] Filed: Feb. 28, 1995

Related U.S. Application Data

[63] Continuation of Ser. No. 68,093, May 28, 1993, abandoned.
[51] Int. Cl.$^6$ .......................... G01N 33/577; C07K 16/44
[52] U.S. Cl. .................. 435/7.93; 530/388.9; 530/391.1
[58] Field of Search ........................ 435/7.93; 530/388.9, 530/391.1

[56] References Cited

U.S. PATENT DOCUMENTS

| | | | |
|---|---|---|---|
| 5,118,612 | 6/1992 | Chu et al. | 435/7.93 |
| 5,126,240 | 6/1992 | Curtiss | 435/7.94 |
| 5,145,790 | 9/1992 | Mattingly et al. | 436/536 |

FOREIGN PATENT DOCUMENTS 0 455 058 A2  11/1991  European Pat. Off. .

OTHER PUBLICATIONS

PCT/US94/05804, PCT Written Opinion, dated Mar. 23, 1995.
E. Sevier et al., Clin. Chem., vol. 27, No. 11, pp. 1797–1802 (1981).
Improvement and Application of an Immunoassay for Screening Environmental Samples for Dioxin Contanimation, Vanderlaan, et al., Environmental Toxicology and Chemistry, vol. 7, pp. 859–870, 1988.
Comparison of Screening Techniques for Polychlorinated Biphenyls in Waste Oils, Carol R. Sutcliffe, et al., Anal. Chem. 1969, 61, 2682–2868.
A Radioimmunoassay for Chlorinated Dibenzo–p–Dioxins, Phillip W. Albro, et al., Toxicology and Applied Pharmacology, 50, 137–146 (1979).
Radioimmunoassay of PCB's in Milk and Blood, William N. Newsome, et al., Intern.J.Environ., Anal.Chem., 1981, vol. 10, pp. 295–304.
Immunoassays in Environmental Analytical Chemistry, Margit Schwalbe–Fehl, pp. 295–303 (1986).
Radioimmunoassay for Quantitiation of 2,3,7,8–Tetrachlorodibenzofuran, Michael I. Luster, et al Anal.Chem. 1980, 52, 1497–1500.
Direct Time–Resolved Fluorosecence Immunoassay of Progesterone in Serum Involving the Biotinstreptavidin System and the Immobilized–Antibody Approach, S.E. Kakabakos, et al., Clinical Chemistry, vol. 38, No. 5, pp. 725–730.
Peroxidase–Labeled Antibody a New Method of Conjugation, Paul K. Nakane, et al., The Journal of Histochemistry and Cytochemistry, vol. 22, No. 12, pp. 1084–1091, 1974.
The Preparation of Peptides Using Mixed Carbonic–Carboxylic Acid Anhydrides, by James R. Vaughn, et al., J. Am. Chem. Soc., vol. 74, pp. 676–673, 1952.
[5] Production of Reagent Antibodies, B.A.L. Hurn, et al., Methods in Enzymology, vol. 70, pp. 104–142, 1980.
Enzyme Immunoassay for the Determination of Atrazine Residues in Soil, K.S. Goh, et al., Bull. Environ.Contam. Toxicol.(1991) 46:30–36.
Determination of Atrazine Residues in Water and Soil by Enzyme Immunoassay, R.J. Bushway, et al Bull.Environ. Contam.Toxicol. (1988) 40:647–654.
Pesticides, Freia Jung, et al., Pestic.Sci., 1989, pp. 303–317.
Enzyme–Linked Immunosorbent Assay Compared with Gas Chromatography/Mass Spectrometry for the Determination of Triazine Herbicides in Water., E.M. Thurman, et al., Anal. Chem., 1990, 62, 2043–2048.
Field Leaf–Test Kit for Rapid Determination of Dislodgeable Foliar Residues of Organophosphate and N–Methyl Carbamate Insecticides, T.C. Blewett, et al., Bull.Environ. Contam.Toxicol. (1990) 45:120–124.
Immunochemical Techniques in Trade Residue Analysis, Chapter 1, Martin Vanderlaan, et al., American Chemical Society, pp. 1–13, 1991.
Reliability of Commericial Enzyme Immunoassay in Detection of Atrazine in Water, Chapter 7, James R. Fleeker, et al., American Chemical Society, pp. 78–85, 1991.
Immunoassay Methods, Jeanette M. Van Emon, Chapter 7, American Chem. Society, pp. 58–64, 1990.
Development of an Enzyme–Linked Immunosorbent Assay for the Analysis of the Thiocarbamate Herbicide Molinate, Shirley J. Gee, et al., J.Agric.Food Chem., 1988, 36, 863–870.
A Radioimmunoassay for Chlorinated Dibenzo–p–Dioxins, Phillip W. Albro, et al., Toxicology and Applied Pharmacology, 50, 137–146, (1979).
Development of a Sensitive Enzyme–Linked Immunosorbent Assay for the Fungicide Fenpropimorph, F. Jung, et al., J.Agric.Food Chem. 1989, 37, 1183–1187.

(List continued on next page.)

*Primary Examiner*—Mary E. Ceperley
*Attorney, Agent, or Firm*—Oblon, Spivak, McClelland, Maier & Neustadt, P.C.

[57] ABSTRACT

An immunoassay method that integrates a sample processing component that enables the testing of a variety of environmental matrixes and the components for performing the method, wherein the immunoassay utilizes a monoclonal anti-PCB antibody to detect the presence or absence of PCB based contamination in a sample when tested in a field or laboratory location.

26 Claims, 2 Drawing Sheets

OTHER PUBLICATIONS

Development of a Monoclonal Antibody Based Enzyme Immunoassay Method for Analysis of Maleic Hydrazide, Robert O. Harrison, et al., J.Agric.Food Chem. 1989, 37, 958–964.

History and Future Outlook of Enzyme Immunoassay, Eva Engvall, History of Future of EIA, pp. 1–3.

Monoclonal Antibodies, Cesar Milstein, Cancer, vol. 49, No. 10, pp. 1953–1957, May 15, 1982.

Chapter 1, Introduction and General Principles, William D. Odell, History of Competative Binding Assays, pp. 1–13.

Scientific Shapping, Onsite Analytical Technology Uses Medical Technology to Detect Organic Content, Kimberly A. Roy, Hazmat World, Dec. 1991.

Monoclonal Antibodies for Dioxin: Antibody Characterization and Assay Development, Stanker et al., Toxicology, 45 (1987) 229–243.

Production and Characterization of Antisera Specific for Chlorinated Biphenyl Species: Initiation of a Readioimmunoassay for Aroclors, Michael I. Luster, Toxicology and Applied Pharmacology 50, 147–155 (1979).

Enzyme Mediated Immunoassay: An Overview, T.T. Ngo, in Enzyme Mediated Immunoassay eds. Debtor et al., Plenum Press; New York, 3 (1985).

Immunoassay Technology for On–Site Testing, Kevin R. Carter, American Environmental Laboratory, Feb. 1992.

Field Analysis Using Rapid Immunoassay Screens, Aisling Scallen, et al., Environmental Lab Magazine.

Recent Developments in the Periodate Method of Conjugating Norseradism Peroxidase (HRPO) to Antibodies, M. Barbara Wilson, et al., Immunofluorescence and Related Staining Techniques, pp. 215–222, 1978.

POLYCHLORINATED BIPHENYLS (PCB) IMMUNOASSAY METHOD, ITS COMPONENTS AND A KIT FOR USE IN PERFORMING THE SAME

This is a continuation of application Ser. No. 08/068,093 filed on May 28, 1993, abandoned.

BACKGROUND OF THE INVENTION

1. Field of the Invention

The present invention relates to methods, compositions and kits for performing PCB immunoassays.

2. Discussion of the Background

Testing is an essential, and integral, component of all environmental protection and restoration activities. It is the rate limiting element that influences the time, cost, and overall efficiency of project management.

The management of toxic waste sites usually involves a progression through the stages of identification, characterization, remediation and monitoring, with testing being performed during each phase. Reference laboratory methods can effectively identify and quantify unknown compounds in a sample, but become relatively inefficient when used to rapidly locate contamination (i.e., mapping), and assist in remediation and monitoring activities. The complexity of laboratory protocols, and the proximity of the labs to the test site, delays the availability of information and increases the cost of data. The ultimate cost is in the time required by the field crews. Effective field screening methods can increase the efficiency of the clean-up process by providing an on-site, high-throughput, and cost-effective way to locate contamination and manage its remediation.

The Environmental Protection Agency (EPA) has long promoted and supported the concept of screening methods to supplement laboratory analysis and increase overall efficiency. The need for more effective methods has been recognized in the Superfund Amendments and Reauthorization Act of 1986 which specifies the development and evaluation of alternative time and cost-saving methods that will assist in the eventual remediation of the nations Superfund sites.

Effective field screening methods can increase the efficiency of site management and improve overall data quality when used to supplement the services of regional laboratories. The development of these methods, however, requires a technology that will be compatible with numerous compounds and matrixes and yet be simple, effective and rugged enough to be incorporated into a protocol for use in the field.

Screening methods need to provide fast, simple, cost-effective and reliable information when operated under field conditions. The reagents and equipment should be portable and stable at ambient conditions, and the claims relating to performance should accurately reflect anticipated field use. The methods should be able to rapidly provide an ample quantity of data, and the protocol should be simple to perform and safe to use. Performance characteristics relative to sensitivity, freedom from matrix interferences and cross-reacting compounds, and correlation to an acceptable reference method should be carefully evaluated. Developers must maintain high, and consistent, quality standards relative to the consistency of their manufacturing protocols, the adequacy of in-process and pre-release quality control methods, and the reliability of their product claims. A necessary characteristic of particular significance for screening methods, is that they exhibit a very low frequency of false negative results.

Screening methods detect contamination at specified concentrations. The concentration may relate to a hazardous threshold, a clean-up target, or a process-control parameter. The potential implications of false negative data far outweigh those of false positive results. The consequence of a false positive, while a costly problem that needs to be minimized, results in additional testing or treatment. False negative data, however, provides an erroneous perception of a clean site, and may have serious environmental and legal consequences. Safeguards that minimize the incidence of false negative results are imperative. Appropriate control over the frequency of false positive data needs to be established and maintained.

The field of immunochemistry,, and the development of immunoassay technology, has been evolving since the late 19th century. However, the majority of these methods have been developed for use by the medical community. These methods have achieved a reputation for reliability and cost-effectiveness. Literally hundreds of immunoassays have been developed for such applications as drug testing, Therapeutic Drug Monitoring (e.g. digitalis derivatives, anti-asthma formulations, anti-epileptic regents, antibiotics), pregnancy testing, hormone testing (e.g., thyroxine, thyroid stimulating hormone), tests for pathological markers (e.g. lactic dehydrogenase isozymes, creatine kinase isozymes), tests for acute phase proteins (e.g., carcinoembryonic antigen, alpha fetoprotein) and tests for tumor marker proteins.

Environmental applications have been explored for the better part of a decade and a number of immunoassay methods have been developed. Most have been used for the detection of herbicides and pesticides in aqueous matrixes. The application of immunoassay technology to the testing of solid waste, complex matrixes, and highly lipophilic compounds, has provided unique challenges for the chemist. The feasibility of developing such methods, however, has been demonstrated with immunoassays for single compounds such as Dioxin (see, for example, Vanderlaan et al, *Environmental Toxicology and Chemistry*, 7:859–870, 1988; and Stanker et al, *Toxicology*, 45:229–243, 1987).

The history of immunoassay technology can be traced to 1900 when Karl Landsteiner described the A, B and Zero (0) blood types after observing the agglutination reaction (i.e., aggregation) that resulted when he mixed the erythrocytes and serum for several of his co-workers on a slide. His observation became the basis for present day blood typing methods. Landsteiner remained a dominant figure in immunology for the next 40 years performing numerous experiments that demonstrated the extraordinary specificity of the antibody binding reaction. He introduced the term "hapten" to define compounds that are unable to directly stimulate antibody production when injected into an animal, but are capable of binding to an antibody if they are produced by an alternate means. Most environmental chemicals are haptens, and although potentially toxic, will not stimulate the immune system to respond.

For 50 years following Landsteiner's discovery, immunoassay technology continued to rely upon the binding and cross-linking ability of an antibody to cause agglutination, cell lysis, and protein flocculation reactions. These methods were relatively insensitive when compared to the immunoassay methods of today, and better suited to the analysis of larger compounds and organisms (e.g. bacteria, proteins). A major advance occurred in the 1950's when Drs. Berson and Yalow, while investigating the metabolism of radio-labelled insulin administered to diabetic patients, observed the production of anti-insulin antibodies in the serum of these patients (see *Principles of Competitive Protein Binding Assays*, Second Ed., Odell, W. D. and Franchismont, P. (Eds.); Wiley and Sons, New York). They described a radioimmunoassay (RIA) method in 1959 that used anti-insulin antibody molecules and radio-labelled insulin in a highly sensitive procedure to quantify insulin levels in the serum. The RIA method used a competitive antibody binding reaction, where radio-labelled insulin and sample insulin compete for a limited number of antibody binding sites. In 1977, Rosalyn Yalow was awarded the Nobel Prize in Medicine for her work on the development of the radioimmunoassay method for peptide hormones (see *Basic and Clinical Immunology*, 7th Ed. Stites, D. P. and Ten, A. I. editors; Appleton and Lange, Conn., 1991). RIA rapidly became a universally accepted method that demonstrated exceptional specificity, sensitivity, and simplicity.

A simpler, safer, and more convenient immunoassay was reported in 1971, when two independent research teams, Engvall and Perlmann, and Van Weeman and Shuurs, simultaneously disclosed a competitive immunoassay method that used an enzyme-labelled conjugate instead of a radio-labelled-conjugate to produce a test that generated a visible end-point signal (see Engvall et al, *Immunochem.* 8:871–874, 1971 and Van Weeman et al, *FEBS Letters*, 15:232–236, 1971). The new ELISA (i.e., enzyme linked immunosorbent assay) method eliminated the problems associated with the safety, disposal and detection of radioactive reagents. The method offered long term stability, the opportunity to generate quantifiable data using instruments commonly available in most laboratories, and a mechanism to develop separation-free (homogeneous) procedures and simple qualitative screening tests.

Current immunoassay technology benefits from the diversity of detection systems developed that use enzyme-catalyzed chromogenic reactions, radionuclides, chemiluminescence, fluorescence, fluorescence polarization and a variety of potentiometric and optical biosensor techniques. Improvements in the sensitivity achieved has necessitated the generation of new descriptive nomenclature for methods that can now detect "zeptomolar" ($10^{-21}$, 600 molecules) concentrations.

Immunoassay methods combine the specific binding characteristics of an antibody molecule with a read-out system that is used to detect and quantify compounds. Antibodies are binding proteins that are produced by the immune system of vertebrates in response to substances that are perceived to be foreign.

The physiological role of antibody, or immunoglobulin, molecules is to bind, and thereby label for destruction, the perceived foreign substance. Antibody molecules are synthesized by a subset of lymphocytes, termed B lymphocytes, that become activated to produce antibody after exposure to substances having prerequisite size, complexity and "foreignness" to the host organism. Antibodies are large, polymeric proteins (i.e. $\geq 1.5 \times 10^5$ d), that can be classified into sub-populations on the basis of their sequence, size and number of subunits. Five major populations, or isotypes, exist carrying the designations of IgM, IgA, IgD, IgG and IgE, with immunoglobulin G (IgG) usually found in the highest concentration.

Immunochemical assays are reliable when used in the screening of soil for contamination and have been used commercially for the rapid analysis of a variety of compounds (see Nqo, in *Enzyme-Mediated Immunoassay*, eds., Debtor et al, Plenum Press: New York, 3 (1985); Odell, in *Principles of Competitive Protein-binding Assays*; eds., Odell et al, J. Wiley & Sons, New York, 1 (1971); *Quantitative Enzyme Immunoassay*; Blackwell Scientifid, Oxford (1978); Engvall, in *Enzyme Immunoassay*, eds., E. Ishikawa et al, Igaku-Shoin, New York, 1 (1981); Jaklitsch, in *Enzyme-Mediated Immunoassay*, eds., Debtor et al, Plenum Press, New York, 33 (1985)), and have been developed to detect a number of different compounds of environmental concern (see *Immunochemical Methods for Environmental Analysis*; ACS Symposium Series 442; Amer. Chem. Soc., Washington, DC (1990); Mapes et al, *Bull. Environ. Contam. Toxicol.* 49, in press (1992); *Immunoassays for Trace Chemical Analysis*; ACS Symposium Series 451, Amer. Chem. Soc., Washington, DC (1990); Harrison et al, in *Biotechnology for Crop Production*, Hedin et al, eds., ACS Symposium Series 379; Amer. Chem. Soc.: Washington, DC, 316 (1988); Hammock et al, in *Recent Advances in Pesticide Analytical Methodology*; Harvey et: al, eds., ACS Symposium Series 136; Amer. Chem. Soc.: Washington, DC, 321 (1980); Van Emon et al, in *Analytical Methods for Pesticide and Plant Growth Regulators* Vol. XXII, 217 (1989); Albro et al, *Tox. & Appl. Pharm.* 50:137 (1979); Blewett et al, *Bull. Environ. Contam. Toxicol.* 45:120 (1990); Bushway et al, *Bull. Environ. Contam. Toxicol.* 40:647 (1988); Fleeker et al, in *Immunoassays for Monitoring Human Exposure to Toxic Chemicals*; Vanderlaan et al, eds., ACS Symposium Series #451 (1991); Gee et al, *J. Agric. Food Chem.* 36:863 (1988); Goh et al, *Bull. Environ. Contam. Toxicol.* 46:30 (1991); Harrison et al, Agric. Food Chem. 37:958 (1989); Jung et al, *J. Agric. Food Chem.* 37:1183 (1989); Jung et al, *Pesticide Science* 26:303 (1989); Thurman et al, *Anal. Chem.* 62:2043 (1990)).

One of the most serious problems in environmental contamination is the presence of polychlorinated biphenyls (PCBs). PCBs, as commercially available, exist as mixtures of PCB congenors containing various mixtures of 209 different isomeric forms. These mixtures were distributed commercially under the commercial name AROCLOR. A number assigned to the AROCLOR designation indicates average percent chlorination of the PCB congenors in the product. Thus, AROCLOR 1260 contains PCBs with an average chlorination of 60%, AROCLOR 1254 has an average chlorination of 54%, AROCLOR 1248 has an average chlorination of 48%, AROCLOR 1242 has an average chlorination of 42%, and AROCLOR 1232 has an average chlorination of 32%. The only one of the important toxic AROCLORs which does not follow the above rule is AROCLOR 1016, which has an average chlorination of 41%. Toxicological data has indicated that the highly chlorinated PCBs are the most toxic to human health. The most frequently encountered toxic AROCLORs are AROCLOR 1260, AROCLOR 1254, AROCLOR 1016, AROCLOR 1232, AROCLOR 1242 and AROCLOR 1248. However, since the composition of PCB products varies from individual product to individual product, from manufacturer to manufacturer within the same product, and even from lot to lot within the same product, immunoassay test development is difficult.

Mattingly et al, U.S. Pat. No. 5,145,790, disclose an immunoassay based method for detecting polychlorinated biphenyls. However, the Mattingly et al method requires the use of a combination of antibodies in order to detect both the highly chlorinated biphenyls, such as AROCLORs 1260 and 1254, as well as the lower chlorinated biphenyls, including AROCLORs 1016, 1221, 1232, 1242, and 1248. Thus, in order to use Mattingly et al in a screening program at a contamination site, one would be required to either test each sample multiple times with different antibodies, or to use mixtures of antibodies in a test.

Under the Toxic Substances Control Act, the U.S. Environmental Protection Agency (EPA) requires the cleanup of all spills and discharges where the spilled material contains more than 50 ppm of PCBS. Contaminated surfaces are required to be cleaned to 10 $\mu$g/100 cm$^2$ or 100 $\mu$g/100 cm$^2$, depending on the nature of the surface. To determine (1) if a cleanup is necessary and (2) whether such a cleanup has been effective, the EPA requires that standard wipe tests be performed on the surface. In 40 CFR 761.123 the EPA defines a "standard wipe test":

> . . . "Standard wipe test" means, for spills of high concentration PCBs on solid surfaces, a cleanup to numerical surface standards and sampling by a standard wipe test to verify that the numerical standards have been met. This definition constitutes the minimum requirements for an appropriate wipe testing protocol. A standard size template (10 centimeters (cm)×10 cm) will be used to delineate the area of cleanup; the wiping medium will be a gauze pad or glass wool of known size which has been saturated with hexane. It is very important that the wipe be performed very quickly after the hexane is exposed to air. EPA strongly recommends that the gauze (or glass wool) be prepared with hexane in the laboratory and that the wiping medium be stored in sealed glass vials until it is used for the wipe test. Further, EPA requires the collection and testing of field blanks and replicates.

In 40 CFR 761.130(e) the EPA also recommends a study by the Midwest Research Institute (MRI) which describes a standard wipe test in more detail. The report proposal leaves a considerable amount of latitude to the analyst as to how the sampling and analysis are to be performed ("Verification of PCB Spill Cleanup by Sampling and Analysis", pp. 41–42).

Thus, an immunoassay method is needed which will provide reliable, accurate and fast results in the field for a wide range of PCB contaminants in a single test using a single antibody, regardless of manufacturer, exact composition or matrix. Such an assay would increase the efficiency of environmental site management activities such as characterization (mapping), remediation monitoring, and regulatory compliance.

In addition, a standard PCB wipe test is needed which will provide reliable, accurate and fast field results in accordance with EPA guidelines.

SUMMARY OF THE INVENTION

Accordingly, one object of the present invention is to provide a PCB immunoassay method which is field compatible, fast and accurate.

A further object of the present invention is to provide a PCB immunoassay method which gives minimal false negative results.

Another object of the present invention is to provide a PCB immunoassay method which detects PCB contamination derived from a wide variety of unknown sources approximately equivalently, where such method is independent of the detection of a single congener in the mixture of PCB congeners, since concentrations of single congeners vary between commercial PCB products.

Another object of the present invention is to provide a PCB immunoassay which is simple to perform and easy to interpret in a field or laboratory setting by operators inexperienced in the art.

Another object of the present invention is to provide an anti-PCB monoclonal (MAb) antibody which is useful in the above-mentioned PCB immunoassay.

Another object of the present invention is to provide an anti-PCB monoclonal antibody with specific reactivity towards PCB mixtures of average chlorination of 32% or higher.

Another object of the present invention is to provide an anti-PCB monoclonal antibody with specific reactivity towards AROCLOR 1260, AROCLOR 1254 and at least one member selected from the group consisting of AROCLOR 1016, AROCLOR 1232, AROCLOR 1242 and AROCLOR 1248.

Another object of the present invention is to provide a reagent (e.g., an enzyme conjugate reagent) for use with the monoclonal antibody in competitive binding type immunoassays.

Another object of the present invention is to provide immunogens which elicit an anti-PCB monoclonal antibody response.

Another object of the present invention is to provide a kit for performing a PCB immunoassay.

Another object of the present invention is to provide a method and kit for performing a PCB immunoassay on a variety of sample matrices, including soil, oil, paint, condensate, water and solid surfaces.

Another object of the present invention is to provide a wipe test and wipe test kit useful in detecting PCB contamination on solid surfaces in accordance with government regulations.

These and other objects of the present invention, which will become apparent from a reading of the description of the invention given hereinbelow, have been found by the inventors to be satisfied by their discovery of a monoclonal antibody which recognizes a molecular characteristic common to multiple components of a variety of PCB products, and to the inventors' discovery of immunogens which can be used to generate such a monoclonal antibody.

The various PCB products, such as the commercially available AROCLORs, differ from each other with regard to their particular chemical composition. The chemical composition of the various AROCLORs has been published by Capel et al, *Chemosphere* 14(5), 439–450 (1985) (for AROCLORs 1242, 1254 and 1260). However, the most toxic have in common specific structural elements, although the relative amounts of each individual congener having the structural element or elements may vary from one PCB product to another. The antibody of the present invention molecularly recognizes the characteristic structural elements common to chemically diverse PCB products with relative equivalency, and can therefore be used to detect the presence of PCBs (contamination) in a sample since the concentration of the pool of characteristic compounds detected by the antibody is relatively constant in chemically disparate PCB products.

The present invention accordingly provides, among its varied embodiments, both an antibody and a test kit which incorporates the antibody. The kit is useful to detect the presence of PCBs (contamination) in a sample because the antibody exhibits approximately equivalent detection of PCB contamination, regardless of product, manufacturer, or diversity of chemical composition, and thereby provides an easy-to-use and highly reliable kit for environmental testing applications.

BRIEF DESCRIPTION OF THE FIGURES

A more complete appreciation of the present invention and many of the attendant advantages thereof will be readily obtained as the same becomes better understood by reference to the following detailed description when considered in connection with the accompanying figures, wherein.

Figure 1:
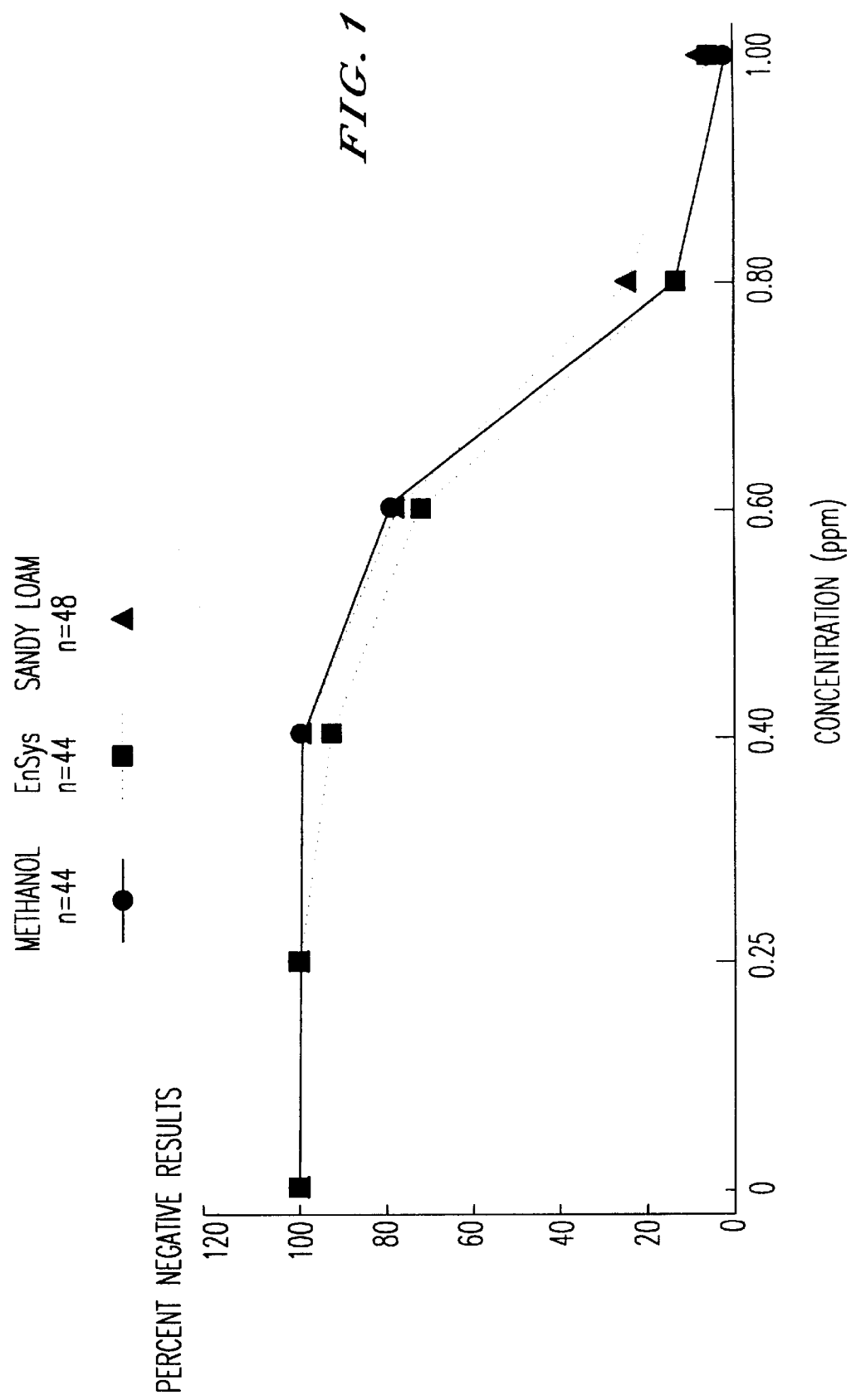
FIG. 1 is a graphical representation of tests performed to measure soil matrix effects on the immunoassay of the present invention between EnSys (a North Carolina clay soil), Sandy Loam and a methanol sample spiked with PCBs.

Both Figures demonstrate the sensitivity and specificity of the assay of the present invention.

DETAILED DESCRIPTION OF THE PREFERRED EMBODIMENTS

In one embodiment, the present invention provides an immunoassay for determining the presence of PCBs (contamination) in a sample (suspected to contain PCBs). The immunoassay comprises:

(i) contacting a monoclonal antibody with specific reactivity towards AROCLOR 1260, AROCLOR 1254 and at least one member selected from the group consisting of AROCLOR 1016, AROCLOR 1232, AROCLOR 1242 and AROCLOR 1248, with a mixture of the sample and a reporter molecule reagent which is cross reactive with the monoclonal antibody, to form an assay mixture;

(ii) incubating the assay mixture to allow competitive binding to the antibody between the PCBs, if present, in the sample and the reagent to form a monoclonal antibody complex; and (iii) detecting the extent of binding of the reporter molecule reagent to the monoclonal antibody and correlating the amount of bound reporter molecule reagent to the amount of PCBs in the sample.

In another embodiment, the invention provides an immunoassay kit which comprises three basic components: (1) a monoclonal antibody with specific reactivity towards AROCLOR 1260, AROCLOR 1254 and at least one member selected from the group consisting of AROCLOR 1016, AROCLOR 1232, AROCLOR 1242 and AROCLOR 1248, (2) a reporter molecule reagent cross reactive with the monoclonal antibody and susceptible to detection, and optionally (3) a signal-generating reagent.

To induce, in a vertebrate host, the formation of the present monoclonal antibodies that can be used to detect the characteristic structural element present in the most toxic PCBs, an immunogen is used which contains a derivative moiety which mimics the structural features of the specific structural element present in these PCBs. The immunogen is synthesized, by standard methods, by coupling a derivative moiety to an immunologic carrier molecule.

Examples of suitable methods include coupling carbohydrates by periodate oxidation and coupling to amines by mixed anhydride chemistry (see Huru et al in *Methods in Enzymology* (Colowick and Kaplan, Eds.) 70:104–142, Academic Press, N.Y. (1980); Wilson et al in *Immunofluorescence and Related Staining Techniques* (Knapp et al, Eds.) pp. 215–224, Elsevier/North Holland, Amsterdam (1978); and Nakane et al, *J. Histochem. Cytochem.* 22:1084 (1974) for periodate methods; and see Erlanger et al., *J. Biol. Chem.* 228:713 (1957); Greenstein et al in *Chemistry of the Amino Acids*, Vol. 2, Wiley, N.Y. (1961); and Vaughan et al, *J. Am. Chem. Soc.* 74:676 (1952) for mixed anhydride methods.

Known immunological carrier moieties can be used, including albumin (e.g., bovine serum albumin), thyroglobulin (e.g., bovine thyroglobulin), hemocyanin (e.g., keyhole limpet hemocyanin), polyamino acids and other molecules having a minimum size, complexity, and foreignness to the host animal. Carriers are usually of the class of proteins, polypeptides or peptides having a molecular weight of at least 1,000 daltons and preferably >10,000 daltons. Carrier molecules may have a reactive group(s) available for covalent conjugation of the derivative. R-groups (e.g., COOH, $NH_2$) of amino acids or sugar moieties of glycoprotein are often used for this purpose in the synthesis of immunogens.

Preferably, the immunogen is a compound of a derivative moiety of the formula

wherein X and Y independently represent a halogen n is an integer from 0 to 5, m is an integer from 0 to 4, wherein n and m cannot both be 0;

$R_1$ is

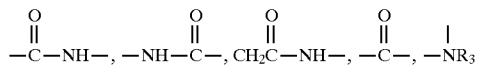

or a single bond $R_2$ is

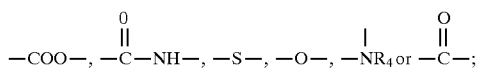

wherein $R_3$ and $R_4$ are each independently hydrogen, $C_1$–$C_2$ alkyls, linear, branched, or cyclic $C_3$–$C_6$ alkyls; and p is 0 or an integer from 1 to 4;

linked to an immunogen carrier molecule.

Preferably X and Y are chloro with n being from 2 to 5 and m being from 2 to 4. A most preferred derivative moiety is

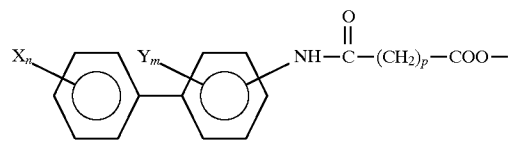

wherein X and Y are chloro, n is from 2 to 5, m is from 2 to 4 and p is 0 or an integer from 1 to 4.

Small environmental chemicals, such as the PCB congenors, by themselves are too small to stimulate an immune response and elicit an antibody response. To elicit an antibody response, derivatives of small molecules, such as a PCB congenor, are attached through a chemical bridge to a much larger "carrier" molecule prior to immunization. According to the invention, the small molecules and accompanying bridge structures of the derivative are designed so that they mimic immunologically at least one common and prevalent congenor present in the PCB molecular pool of the most toxic AROCLORs. A number of modifications to the bridge structure ($R_1$—$(CH_2)_p$—$R_2$) are possible and can produce similar results. Any vertebrate is a suitable host for the immunization procedure, such as mice, rats, dogs, pigs and other domestic animals, with mice being preferred. Additionally, in vitro immunization can be used, with animal cells, including human cells, as the immunization host.

The immunoassay method of the present invention uses a hybridoma-derived, monoclonal antibody. The monoclonal antibody is selected using a multi-parameter screening process. A reactive panel profiling system is developed to identify and select appropriate cell lines and monoclonal antibodies on the basis of sensitivity, PCB product recognition characteristics, and freedom of interference from confirmed negative soil samples or cross-reacting compounds. The candidate monoclonal antibody reagents are characterized by their ability to selectively bind to a defined pool of molecules having the specific structural element, which are present in targeted PCB products (e.g. the various AROCLORS). The selected antibody allows the method to rapidly detect toxic PCB contamination, regardless of manufacturer or chlorination level, at, or above, the regulatory level (i.e., a concentration of 1 ppm in soil at a >95% confidence level), with lower concentrations detectable at lower confidence levels. The antibody operates through the selective recognition of a specific molecular structure element found in a plurality of compounds present in all PCB compositions.

The reagent of the present invention, preferably containing a hapten and a reporter moiety, which in a referred embodiment is an enzyme conjugate reagent, is cross reactive with the monoclonal antibody and capable of providing a detectable change in the sample solution being assayed, either alone or in combination with a co-reagent. Preferably, the hapten-reporter reagent comprises a compound of formula

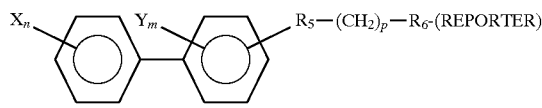

wherein X and Y independently represent a halogen n is an integer from 0 to 5, m is an integer from 0 to 4, wherein n and m cannot both be 0;

$R_5$ is

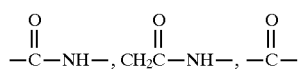

or a single bond $R_6$ is

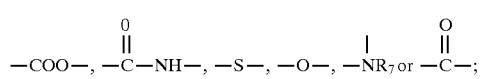

wherein $R_7$ is hydrogen, $C_1$–$C_2$ alkyls, linear, branched, or cyclic $C_3$–$C_6$ alkyls; and p is 0 or an integer from 1 to 4;

linked to a reporter molecule.

A preferred enzyme (reporter moiety) for use in the enzyme-conjugate reagent of the present invention includes an enzyme selected from the group consisting of horseradish peroxidase, alkaline phosphatase, β-galactosidase, glucose oxidase, G6-PDH (glucose-6-phosphate dehydrogenase) and urease, with horseradish peroxidiase being most preferred.

A more preferred enzyme conjugate reagent is a compound of formula

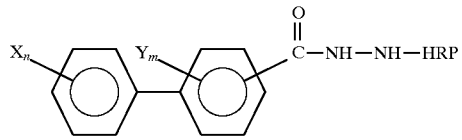

coupled to horseradish peroxidase (HRP).

The enzyme conjugate is prepared using conventional methods. Illustratively, numerous functional groups on enzyme molecules (e.g. amino, sulfhydryl, carboxyl, carboxamide, tyrosyl, sugars) offer convenient points for the attachment for the ligands. As is known, enzymes enhance the sensitivity of the method by the catalytic amplification of the detection signal. A single molecule of the enzymes commonly used in immunoassay methods will convert approximately 106 molecules of a substrate into a product within one minute at ambient temperatures. Catalysis is a function of the conformation at the enzyme's catalytic site, and it is this conformation, and the alignment of certain amino acid residues at spatially significant positions, that influences its rate and selectivity. The catalytic site is maintained by non-covalent (i.e. hydrophobic, hydrogen bonding, ionic and Van der Waals interactions) and covalent (i.e. disulfide) forces, and can be influenced by temperature, the binding of ions, chaotropic agents, detergents, lipids, etc.. It is therefore important to normalize and correct for anticipated variations in the reaction environment.

The enzyme conjugate of the present invention must be cross-reactive with the anti-PCB antibody of the present invention and capable of inducing a detectable change in the sample by reaction with a signal producing substrate or reagent used in the immunoassay.

The immunoassay-based system of the present invention uses a signal producing reagent which, upon reaction with the bound enzyme conjugate/antibody complex after incubation, provides a detectable signal indicating the presence or absence of PCB contamination in the sample being tested. Suitable signal producing reagents include a hydrogen peroxide/tetramethyl benzidine pair, or a hydrogen peroxide/phenylene diamine pair, in combination with an enzyme conjugate reagent containing horseradish peroxidase, o-nitro-β-D-galactopyranoside (ONPG) in combination with an enzyme conjugate reagent containing β-galactosidase, o-nitrophenylphosphate in combination with an enzyme conjugate reagent containing alkaline phosphatase and glucose in combination with glucose oxidase or G6-PDH. The method of the present invention preferably uses the combination of a hydrogen peroxide ($H_2O_2$) substrate solution with a tetramethylbenzidine (TMB) chromogen, with the combination producing a blue chromophore upon oxidation of TMB by $H_2O_2$.

An important characteristic of the immunoassay of the present invention, as well as with any field screening method, is the minimization of false negative results without producing excessive false positive data. Statistically, therefore, the standard concentration should not be set at the concentration of interest, but below it. Setting the standard concentration to coincide with the desired detection concentration would result in a 50% false negative incidence at that desired concentration. To minimize this effect, standards used in the immunoassay of the present invention should be offset below the target concentration to produce a >95% confidence level of detecting contamination at, or above, the desired level. For example, to obtain a method which gives results having a >95% confidence level for detection of PCBs at 5 ppm, a 2.5 ppm standard could be used. The standard is set below the target level. The actual concentration of standard used is a function of the dose-response characteristics of the assay and the overall interference and precision of the method.

Immunoassay methods have conventionally been used to test liquid matrixes such as blood, urine, and water. This method is designed to test also liquid oil-based matrices, solid matrices and solid surfaces. However, the testing of liquid oil-based matrices and solid matrices requires that the issues of sample collection, dispersion, extraction and clarification be addressed and integrated with the immunoassay component.

While the assay of the present invention may be performed on samples of a wide range of qualities, a reproducible, particulate-free, extract is preferred for optimum results. The extraction and recovery of a compound from soil requires the selection of an appropriate solvent system, adequate sample dispersion, sufficient time for partitioning, non-invasive clarification and compatibility with the subsequent immunochemistry. However, current sample processing by analytical methods utilizes solvents that are incompatible with immunochemical methods and is slow and expensive.

One suitable method for soil sample preparation involves the collection of a 10 g sample measured with a small battery-operated balance. The sample is then transferred into a dispersion vial containing a suitable organic solvent, such as methanol, and conventional dispersing pellets, and is subjected to a one minute manual agitation for adequate dispersion and partitioning of the analyte into the solvent. Filtration of the sample suspension to produce a particulate-free extract can be accomplished using a fingertip-operated filter unit fitted with non-adsorbing filters. The clarified extract is then ready for testing with the immunoassay of the present invention following dilution or other removal of the solvent. Solvent-resistant antibody reagents could be used to eliminate or limit the need for the solvent or dilution step.

Buffers, detergents (e.g. Tweens, Tritons, etc.) or solvents, used alone, or in combination, have proven to be effective for extraction from soil samples. Analytical methods for the analysis of solid waste rely upon gravimetrically collected samples, and results are reported in gravimetric units. Volumetric sampling for solid waste should preferably be avoided because of the potential bias (up to 200%) that may be caused by the specific gravity of the sample.

The present immunoassay method permits the simultaneous testing of soil samples for contamination at multiple concentrations to facilitate the construction of contamination contour profiles. The method is preferably for screening purposes and several safeguards have been incorporated to minimize the incidence of false negative results.

Common oil-based matrices for PCBs include transformer oils such as mineral oils and non-PCB dielectrics, motor oils, silicone oils, fuel oils, organic solvent waste streams of synthetic processes, chlorinated solvents from the dry cleaning and electronics industries, gas pipeline condensates and phthalate ester based oils, as well as aqueous based paints and condensates that contain oil-based contaminants. The EPA requires used oils which are destined for recycling to contain less than 2 ppm PCBs, while waste oils or solvents destined for incineration must contain less than 50 ppm PCBs. Unfortunately, most of the above oil-based matrices contain oils or solvents which are incompatible with aqueous immunochemistry methods. Accordingly, one embodiment of the present invention provides a sample processing component for use in preparing samples from oil-based matrices, such as those listed above, for use in the PCB immunoassay of the present invention.

Due to the lipophilic nature of PCBs, it is extremely difficult to remove the PCBs from oil-based matrices by mere extraction. In order to remove the PCBs from the oil-based matrices, a solvent must be used which: (1) is immiscible with alkanes, especially higher molecular weight alkanes and (2) provides efficient partitioning of PCBs from the matrix. Since extraction alone has proven unacceptable, the extraction solvent must also be compatible with the following processing operations: (1) resistant to attack from strong acids, oxidants, alkali and reducing agents, (2) have utility in chromatographic methods, especially normal phase thin-layer chromatography (TLC) on silica plates and (3) have sufficient volatility or susceptibility to analyte reconcentration methods. A suitable solvent which meets all of the above requirements is acetonitrile.

In order to remove PCBs from oil-based matrices in a manner which provides a workable immunoassay using the method of the present invention, a multistep sample processing protocol is used. The processing protocol comprises:

(1) Extraction of the oil-based sample with the extraction solvent, preferably acetonitrile, in a volume ratio of solvent to sample sufficient to balance sensitivity desired (provided by small extraction solvent volumes) with matrix variability (compensated by large extraction solvent volumes). The preferred volume ratio of solvent to sample is approximately 9:1.

(2) Oxidation of a portion of the extract obtained, by treatment with an oxidizing agent and an acid. Suitable oxidizing agents include chromates, permanganates, periodates, persulfates, cerium (IV) salts, cobalt (III) salts and manganese (III) salts, with ceric ammonium nitrate being preferred. Suitable acids include the strong mineral acids with sulfuric, perchloric, nitric and tetrafluoroboric acids being preferred, with 0.5 to 1.0 ml, preferably 1.0 ml, of 70% $HClO_4$ used per 1 ml of extract in a most preferred embodiment.

(3) Quenching and concentrating the oxidized extract by combining the oxidized extract with about 4 volumes of an aqueous salt solution, wherein the aqueous salt solution is preferably a solution of sodium chloride, sodium sulfate or sodium nitrate at a concentration of from 2M to 5.5M, followed by extraction into 0.1 volumes of a suitable solvent which is immiscible with the salt solution, such as linear, branched or cyclic hydrocarbon solvents having from 5 to 8 carbons or methylene chloride, with isooctane being most preferred. This extraction procedure is a modification of the procedure of Jenkins et al *Anal. Chem.* 63, 1341 (1991).

(4) Chromatographing the resulting isooctane solution using normal phase chromatography, preferably normal phase TLC, for example, on a chromatographic plate having as a chromatographic medium a member selected from silica, fluorosil, alumina and bonded phase silica, with silica being preferred, using a suitable developing solvent, which preferably gives retention factors ($R_f$s) for the various AROCLORs of from 0.32 to 0.68. A preferred elution solvent is a linear, branched or cyclic volatile hydrocarbon solvent having from 5 to 8 carbons, with isooctane being most preferred. In a preferred embodiment the TLC plate is preeluted with methanol to remove possible interfering substances from the plate, prior to elution of the sample. After development of the chromatographic medium (e.g., the TLC plate), the plate is extracted with methanol to remove the PCBs and the methanol extract is subjected to the immunoassay of the present invention.

When testing samples containing these types of matrices without the above processing protocol, the presence of turbidity in the first step of the immunoassay is an indicator for possible false negative results. Thus, if the buffer solution of the first step becomes turbid on addition of the sample, a negative result should be viewed with caution.

The basic characteristics of specificity and equivalent detection of the assay of the present invention are a result of the monoclonal antibody (MAb) and the reporter molecule reagent. The assay provides approximately equal recognition of a variety of PCB products (e.g., the various AROCLORs), approximately equal recognition of PCBs from different manufacturers having different chemical compositions and with different chlorination levels, low cross-reactivity with unrelated compounds and is not significantly affected by normally found constituents of negative soil extracts.

Conventional hybridoma techniques are employed to prepare the anti-PCB monoclonal antibody (MAb) for the assay of the present invention, by the use of the immunogen reagent of the present invention. The method for producing MAbs is extremely powerful and allows for the preparation of a defined and reproducible Ab reagent with a unique, chosen specificity (see Milstein, Cancer, 49:1953–1957, (1982)). The production of polyclonal antisera is much less controlled since polyclonal antisera are the product of numerous Ab populations having varying specificity and sensitivity characteristics. An immunoassay for PCB products has been developed using polyclonal antisera, but has been shown to exhibit a number of problems, such as variability in specificity and recognition requiring very lengthy sequential protocols. MAbs are also homogeneous with a defined specificity, unlike polyclonal antisera which contain a mixed population of antibodies. Hybridoma cell lines are immortal when stored under appropriate conditions and provide access to an unlimited supply of MAb reagent that provides performance characteristics to the test system that will be exactly the same from lot to lot.

A unique strategy is used for antibody production. This strategy involves developing an antibody to one or more specific structural elements that are present on a defined set of compounds in PCB products. Because of the chemical complexity of PCB products and the tendency of the composition to vary between products and among manufacturers, the antibody is designed to recognize defined structural elements present in compounds contained in each of the various AROCLOR compositions. Recognition of a panel of compounds, containing the defined structural elements instead of a single compound, allows the assay of the present invention to average out the concentration difference of any single component present in the different types of PCB products. Additionally, recognition of a collection of compounds rather than a single constituent contributes significantly to the sensitivity of the assay.

Preferably the pool of compounds selected for detection by the assay are predominantly a PCB congenor chlorinated with 4, 5 or 6 chloro groups.

The immunogen of the present invention is used to immunize suitable hosts, such as mice.

Hosts responding to the immunization protocol are selected as splenocyte (or lymphoid cell) donors for hybridoma production. A culture of immune splenocytes in a defined tissue culture medium, such as HAT, with conventional modified myeloma cells, capable of providing a hybridoma, provides the fusion products s—s, s-m, and m—m (with s=splenocyte and m=myeloma cell). Within tissue culture medium the s—s fusion product normally has a short lifetime and dies within days. Also, the m—m fusion product has a very short lifetime in the tissue culture medium used, lacking the metabolic components needed for DNA synthesis. However the s-m fusion product (or hybridoma) survives in tissue culture and retains the Ab-producing characteristics of the s,plenocyte parent, and the high rate of growth and relative immortality of the myeloma cell parent. This hybridoma cell line replicates itself readily in culture producing daughter cells that provide a reproducible, homogeneous, and consistent supply of the monoclonal anti-PCB antibody of the present invention.

The structure of the reporter molecule reagent can have a significant influence on immunoassay performance. Both the derivatized ligand and the bridge play an important role in antibody binding. Antibody and reporter molecule reagent pairs should be able to satisfy the following criteria:

Recognition and displacement and prerequisite sensitivity for AROCLORs and other PCB products in a sample Low cross-reactivity to non-related compounds Approximately equal sensitivity for different PCB products, i.e., toxic AROCLORs Insignificant negative soil matrix effects Antibody and reporter molecule reagent pairs which best satisfy the above criteria are most suitable for the assay of the present invention.

The immunoassay of the present invention is performed according to the following procedure. Monoclonal anti-PCB antibody is immobilized in an assay vessel, or other solid support, preferably to the bottom of a polystyrene tube, at a concentration, of from 0.005 to 20 µg/tube, preferably 0.1 to 0.4 µg/tube. The concentration and affinity of the antibody for the sample molecules and reporter reagent molecules directly influences the overall sensitivity of the final method. High, equivalent, affinity, and minimal non-specific signal generation, produces assays having superior sensitivity, with affinity binding constants, Ka, from $10^4$–$10^{12}$ L/mol, preferably $10^4 10^9$ L/mol.

The assay of the present invention compares a sample to be tested with a standard solution containing a compound cross-reactive with the antibody of the present invention, which is present in the standard solution in an amount sufficient to provide a 95% confidence level for detection at the desired level.

By way of example, the following describes a simultaneous test of a negative sample, a sample containing $\geq 5$ ppm of PCBs, and a standard solution containing the equivalent of approximately 2.5 ppm of AROCLOR 1248. Initially, following extraction from soil, the sample extract and standard are added to separate, and identical, antibody-coated test tubes. To each tube is added an equal volume of the reporter molecule reagent solution. The tubes are then allowed to incubate at ambient conditions for approximately ten minutes.

During the incubation period sample molecules and reporter reagent molecules compete for the limited number of antibody binding sites that are available on the bottom of each of the tubes. The antibody concentration present is insufficient to permit the binding of all of the sample and reporter reagent molecules simultaneously, and a situation somewhat analogous to the game of musical chairs exists, with the limited antibody binding capacity serving as the chairs in this example. The concentration of reporter molecule reagent immobilized in each tube after incubation is inversely proportional to the concentration of PCBs in the sample or standard. The standard in the Standard tube limits the binding of reporter molecule reagent, the Negative sample permits more reporter molecule reagent to bind (relative to the standard), and the positive sample limits the binding of the reporter molecule reagent (relative to the standard). At the end of the 10 minute incubation period, the tubes are washed leaving only the reporter molecule reagent that was retained by the immobilized antibody on the bottom of each tube.

The bound reporter molecule reagent/antibody complex remaining is next used to produce a detectable signal. Upon addition of a signal forming reagent, preferably a substrate/chromogen reagent, the enzyme molecules catalyze the formation of a detectable signal. The signal that is generated is directly proportional to the concentration of reporter molecule reagent present. A preferred substrate/chromogen reagent is $H_2O_2$, and tetramethyl-benzidine (TMB) which, when used with a preferred reagent wherein the reporter molecule is the enzyme horseradish peroxidase, reacts with the enzyme portion of the reagent, facilitating the oxidation of TMB by $H_2O_2$ and generating a blue color.

Thus, the negative sample tube rapidly produces a solution that is visibly darker (i.e. greater absorbance) than the standard tube. The positive test sample produces a solution having less color (i.e. lower absorbance) than the standard tube. By comparing the signal of the sample tubes to the signal of the standard tube using a battery-operated comparative photometer, optionally included with the kit of the present invention, samples containing greater than or equal to the desired level of contamination can be detected with >95% confidence. In this competitive ELISA method the final absorbance is inversely proportional to the ligand concentration present in the test sample.

The assay method of the present invention can process multiple samples in less than 30 minutes. The method is self-contained, field-compatible and does not require refrigeration or use hazardous components. The detection level can be set at the users discretion, with 0.3 ppm as the maximum sensitivity obtainable with the current configuration using a solid matrix sample and 15 ppb for aqueous samples.

The kit of the present invention may be configured for analysis of soil samples, oil matrix samples, aqueous samples, and solid surfaces. The kit of the present invention contains five basic components: (1) a sample processing component for preparing the sample for testing by the assay method (described above for soil samples), (2) at least one assay vessel, preferably a plurality, containing an amount of an immobilized anti-PCB monoclonal antibody, equivalent amounts when a plurality of vessels is used, (3) a standard solution containing a specific level of PCBs in a suitable solvent, (4) a reporter molecule reagent which is reconstituted to form a solution containing a reporter reagent which is cross-reactive with the monoclonal anti-PCB antibody, in a suitable solvent, where the reporter reagent is preferably a lyophilized enzyme-conjugate reagent, and (3) means for forming and detecting a signal indicating the presence or absence of PCB based contamination in the sample being tested. Optionally, the kit contains one or more of the following additional components: (6) wash solutions for performing the wash step of the assay method, (7) weighing boats into which the sample is weighed using (8) a battery-operated scale, (9) one or more filters for preparing a clarified extract sample, (10) one or more dilution vials, (11) substrate solution and (12) stop solution to halt signal formation by the signal-forming reagent. Preferably the assay is provided in a coated-tube format in which the means for forming and detecting a signal comprises the use of a substrate/chromogen reagent which forms a detectable colored signal with the level of PCB contamination determined by comparison of the color developed by the test samples to the color of the kit standard. In order to eliminate temperature variations, timing errors and operator mistakes, the standard is preferably run in parallel with the samples. Therefore, any assay variations will equally affect both the standard and the samples. Using this format with the standard run in parallel, the assay has the following characteristics:

1. The sensitivity as currently configured for soil samples is 0.35 ppm for AROCLOR 1260, 0.33 ppm for AROCLOR 1254, 1.00 ppm for AROCLOR 1248, 1.57 ppm for AROCLOR 1242, 3.25 ppm for AROCLOR 1232 and 3.50 ppm for AROCLOR 1016.
2. Different soil matrices cause little interference in the assay.
3. The test is reproducible from lot-to-lot, day-to-day, and person-to-person.
4. The assay is operable over a temperature range of 4°–30° C., preferably 15°–30° C.
5. Storage at room temperature (up to 30° C.) is acceptable.

The immunoassay of the present invention has many advantages, including field screening compatibility, speed in obtaining a result, and a lack of false negative results. Specific characteristics had to be integrated into the method in order to achieve these advantages. The first was to minimize the incidence of false negative results. A false negative test does not detect a contaminated sample and therefore, can be potentially dangerous both to the customer and the environment. A false positive, on the other hand, might be inconvenient but not dangerous. Therefore, the immunoassay of the present invention was designed to detect positive solid matrix samples containing $\geq 1$ ppm of PCBs with a minimum of false negative results. This is accomplished by using a standard containing the equivalent of AROCLOR 1248 in soil at 0.7 ppm to detect 1 ppm PCB with a 95% confidence level. Preferably, two standards are tested simultaneously with each assay, both to minimize false negative results and to provide an internal quality control parameter to control for the integrity of the chemistry and performance of the operator.

The immunoassay has also been simplified by making it a semiquantitative test using a standard at a single concentration. The use of one standard concentration greatly simplifies the test protocol and eliminates the data manipulation and expensive instrumentation that are normally necessary for quantitative tests. The test becomes a semiquantitative "yes/no" test that determines whether a sample contains greater or less than a set level of PCB contamination, depending on the concentration of the assay standard. The use of multiple standards at varying concentrations allows one to perform a quantitative assay by comparison to the signals produced by the samples on a concentration vs. signal plot.

In the wipe test of the present invention, the sample processing component (1) is an extraction vessel containing an extraction solvent and a wiping means. In addition to the extraction vessel and its contents, the wipe test also includes a wipe template which provides a controlled surface area to be wiped by the wiping means.

The extraction vessel may be made from any suitable material which is nonreactive with the extraction solvent contained therein. Suitable extraction solvents include lower alcohols, such as methanol, ethanol, and isopropanol with methanol being preferred. The extraction solvent used must not leach interfering substances from the wiping means. The wiping means may be a woven or nonwoven cloth material made from synthetic or natural fibers, which are inert in the presence of the extraction solvent and PCBs.

Cotton gauze or glass wool are preferred, with the preferred size being 4 in by 4 in. A suitable wiping means is made from DURX 670, sold commercially by Berkshire Manufacturing Co.

The wipe template is used to provide a controlled surface area for wiping in order to correlate with the EPA requirements, noted above. While the wipe template may provide any surface area as the controlled area, it is preferred that the template specifically define a 100 cm$^2$ area, preferably of dimensions 10 cm×10 cm. Use of other surface area templates would require correction of the results obtained in order to correlate to the EPA standard.

In performing the wipe test with the assay of the present invention, the wiping means is removed from the extraction vessel and excess solvent is squeezed from the wiping means back into the vessel. The wipe template is held against the surface to be tested and the exposed surface is wiped using the wiping means. When the wiping means is a 4 in by 4 in cloth, the surface is wiped using both sides of the wiping means. The wiping means is then returned to the extraction vessel and the vessel recapped and shaken to extract the PCBs from the wiper. A sample of the extract is then decanted and filtered before use in the immunoassay of the present invention. The wipe test of the present invention provides a positive result whenever a surface wipe recovers 10 $\mu$g of PCBs from 100 cm$^2$ of surface, thus meeting or exceeding the EPA requirements. In developing the PCB wipe test, it was desired to adapt the wipe procedure to the PCB immunoassay of the present invention without any modifications to the immunoassay procedure. This is accomplished by correlating any matrix effects in the wipe and soil tests. No systematic differences between the wipe matrix and various soil matrices were found.

The immunoassay of the present invention makes possible the rapid screening of numerous samples in the field at the site. The rapid, on-site screening of multiple samples is a significant advantage compared to the standard analytical GC or IR methods. The quick screening of samples allows quick answers to important questions concerning the project, such as, the area of contamination, has the area been remediated to acceptable levels, and does additional contaminated material need to be removed? With the immunoassay method of the present invention, personnel, time and equipment can be used more cost-effectively.

Having generally described this invention, a further understanding can be obtained by reference to certain specific examples which are provided herein for purposes of illustration only and are not intended to be limiting unless otherwise specified.

EXAMPLE

Example 1

Preparation of Assay Components Preparation of Monoclonal Antibody

Female Balb/c mice received a primary subcutaneous immunization with 50 ug of PCB derivatized to bovine serum albumin in adjuvant (MPL+T DM Emulsion, RIBI Immunochem Research, Inc., Hamilton, Mont.). Subcutaneous secondary injections (25 ug) were given at day 21, 35, and then monthly. The production of monoclonal antibodies was performed according to conventional procedures (see Milstein, Cancer, 49:1953–1957 (1982)). Hybridoma cultures producing monoclonal antibodies recognizing free hapten by EIA were cloned by limiting dilution. Clone F40-11G6 was selected based upon sensitivity, PCB product recognition characteristics and freedom of interference from confirmed negative samples or cross-reacting compounds. This clone was deposited, in accordance with the Budapest Treaty, with the American Type Culture Collection (ATCC) on Oct. 28, 1997 as ATCC No. HB-12421.

Horseradish peroxidase conjugate reagent

Horseradish peroxidase (HRP) conjugate reagent was prepared with a hydrazide derivative of 2',4'-dichlorobiphenyl-1-carboxylic acid using the conventional periodate method (see Nakane et al J. Histochem. Cytochem. 22:1084 (1971)).

Antibody Coated Tubes

Antibody coated tubes were prepared by passively coating polystyrene (12×75 mm, NUNC) tubes with the monoclonal F40-11G6 antibody diluted in PBS and incubating overnight.

Example 2

PCB Immunoassay Procedure—1 ppm in Soil

The immunoassay method of the present invention has been demonstrated as follows:

10 g of a soil sample were placed in an extraction vial containing 20 mL of methanol and 5 steel pellets (6mm) and the vial and its contents shaken for 1 minute to disperse the soil particles and extract the PCB. The sample was then filtered to clarify the sample using a filter of glass fiber and 0.45$\mu$ Teflon. 45 uL of the clarified filtrate sample was mixed with 955 $\mu$l of 10 mM PBS (pH=7.4) and the resulting mixture added to lyophilized enzyme conjugate reagent (0.3 $\mu$g) and mixed. At the same time, 2×45 uL of the AROCLOR 1248 standard are similarly treated. The sample and the two standards were then poured into three identical antibody coated tubes, respectively, and the resulting solution mixed. The resulting solution was incubated for 10 minutes at ambient temperature and then washed 4× with a wash buffer (detergent-saline solution). 250 uL of tetramethylbenzidene solution (KP Laboratories, Cat. No. 50-76-02) was added along with 250 uL of hydrogen peroxide solution (KPL, Cat. No. 50-65-02) and the resultant solution mixed. After incubating for 2.5 minutes the color development reaction was stopped with 250 uL of stop solution (1M sulfuric acid).

The optical density (OD) of the test sample was compared to the OD of the AROCLOR 1248 standard (0.7 ppm) which was tested simultaneously with the sample. If the sample OD is less than the standard OD, the sample contains greater than 1 ppm PCBs. If the sample OD is greater than the standard OD, the sample contains less than 1 ppm PCBs. Other concentration ranges can be assessed by diluting the test samples with suitable diluents, as long as they are non-reactive with the components of the assay.

The sensitivity of the soil test was established to be 1.0 ppm for PCB in soil with >95% confidence for AROCLOR 1248. To develop the test for detection at this level, the concentration of AROCLOR 1248 in the kit standard was set to coincide with the mid-point of the immunoassay dose response curve, the most precise portion of the curve. Also, the antibody concentration immobilized on the tubes and the sample dilution protocol were adjusted so that samples containing 1 ppm or more PCBs were positive (i.e. lower absorbance) versus the absorbance of the kit standard.

Matrix interference in soils was assessed by determining the assay sensitivity (recovery of spiked samples) in soil extracts confirmed to be negative by GC analysis. Since the sensitivity of the assay was barely changed when spiked negative extracts were compared to spiked methanol samples (FIG. 1), it was concluded that there was negligible soil matrix interference.

Another criterion, in demonstrating the performance of the assay of the present invention, was to determine the sensitivity to other cross-reacting compounds commonly found at PCB sites and compounds having similar structures.

These compounds were tested for their reactivity with the present 1 ppm PCB immunoassay. Table 1 shows the results obtained, the concentration providing a positive result compared to the kit standard and the calculated percent cross-reactivity. Overall, the compounds were each less than 1% cross-reactive, with one exception at 2%, indicating high-specificity for PCBs in the present method.

TABLE 1

CROSS-REACTIVITY TABLE

| COMPOUNDS | CONCENTRATION GIVING A POSITIVE RESULT; SOIL EQUIVALENT (PPM) | PERCENT CROSS-REACTIVITY |
|---|---|---|
| BENZENE | >10,000 | <0.01% |
| 1-CHLORONAPHTHALENE | >10,000 | <0.01% |
| O,P-DDT | >10,000 | <0.01% |
| 9,10-DICHLORO-ANTHRACENE | >10,000 | <0.01% |
| DIESEL | >10,000 | <0.01% |
| ENVIROTEMP | >10,000 | <0.01% |
| GASOLINE | >10,000 | <0.01% |
| HEXACHLOROBENZENE | >10,000 | <0.01% |
| METHYLENE CHLORIDE | >10,000 | <0.01% |
| NAPHTHALENE | >10,000 | <0.01% |
| PENTACHLOROBENZENE | >10,000 | <0.01% |
| PENTACHLOROPHENOL | >10,000 | <0.01% |
| R-TEMP | >10,000 | <0.01% |
| TRICHLOROETHYLENE | >10,000 | <0.01% |
| 2,4,6-TRICHLOR-p-TERPHENYL | >10,000 | <0.01% |
| XYLENES | >10,000 | <0.01% |
| 2,4-D | 1,000–10,000 | <0.1% |
| HALOWAX 1013 | 1,000–10,000 | <0.1% |
| HALOWAX 1051 | 100–1,000 | <1% |
| BIFENOX | 100–1,000 | <1% |
| 2,4-DICHLOROPHENYL BENZENESULFONATE | 100–1,000 | <1% |
| SILVEX | 100–1,000 | <1% |
| 1,2,4-TRICHLOROBENZENE | 100–1,000 | <1% |
| 2,4-DICHLORO-1-NAPTHOL | 50 | 2% |
| TETRADIFON | 10–100 | <10% |

AROCLOR Recognition

Dose response curves were generated using the various commercial AROCLOR compositions. Table 2 shows the results of 3 sets of duplicate dose response curves and the mean ED50 obtained for each sample.

TABLE 2

AROCLOR SENSITIVITY COMPARISON PCB MONOCLONAL TEST

|  | 1260 | 1254 | 1248 | 1242 | 1232 | 1016 | 1221 |
|---|---|---|---|---|---|---|---|
| DETERMINATION 1 | 34.20 | 32.10 | 95.20 | 176.00 | 324.00 | 352.00 | 4,174.00 |
| 2 | 32.00 | 34.60 | 104.50 | 160.00 | 377.00 | 346.00 | 4,013.00 |
| 3 | 36.40 | 29.00 | 92.90 | 122.00 | 251.00 | 325.00 | 5,354.00 |
| MEAN ED50 (ppb) | 34.20 | 31.90 | 97.50 | 153.00 | 317.00 | 341.00 | 4,514.00 |
| STD DEV | 2.20 | 2.81 | 6.14 | 27.74 | 63.26 | 14.18 | 732.19 |
| SENSITIVITY | 0.35 | 0.33 | 1.00 | 1.57 | 3.25 | 3.50 | 46.28 |

Example 5

Figure 2:
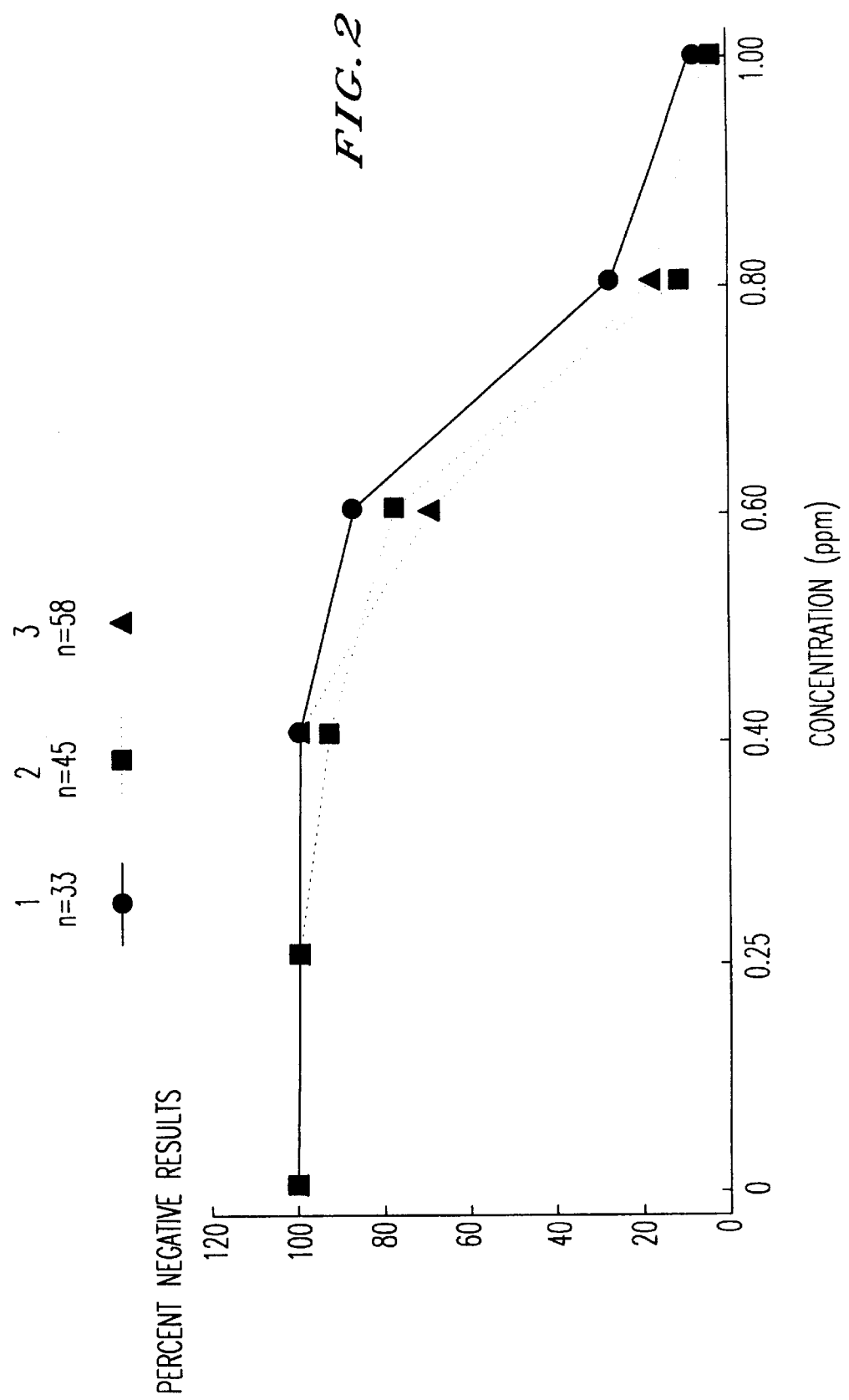
FIG. 2 is a graphical representation of tests performed to measure variability between different operators in performing the immunoassay of the present invention.

Reproducibility from person-to-person, day-to-day, and lot-to-lot was investigated. Using sensitivity profile data accumulated from three lots, comparisons of three trained operators were made (FIG. 2). This graph illustrates insignificant changes in specificity and sensitivity at the negative and 1 ppm levels. Another measure of operator variability is the reproducibility of the standard pairs, specifically the difference in OD units between the two standards (see Table 3)

TABLE 3

OPERATOR VARIABILITY,
REPRODUCIBILITY OF STANDARD PAIRS

| OPERATOR | NUMBER OF OBSERVATIONS | MEAN DIFFERENCE BETWEEN STDS | STANDARD DEVIATION |
|---|---|---|---|
| 1 | 59 | 0.058 | 0.059 |
| 2 | 67 | 0.060 | 0.057 |
| 3 | 82 | 0.073 | 0.053 |

These results indicate no difference in reproducibility for trained operators.

Untrained Operators

This study had two purposes: 1) to determine if variation exists that causes differences in the interpretation of the test and 2) if the test is "useable" for the untrained operator.

Five operators, unfamiliar with running the test, were recruited to assay four sensitivity profiles consisting of a pair of kit standards, 0 ppm, 0.25 ppm and 1.0 ppm (see Table 4). The tests (n=20) resulted in no false positives at 0 or 0.25 ppm and 5% false negatives (1 false result out of 20) at 1.0 ppm.

TABLE 4

UNTRAINED OPERATORS; VARIABILITY

| OPERATOR | 1 | 2 | 3 | 4 | 5 |
|---|---|---|---|---|---|
| N = | 4 | 4 | 4 | 4 | 4 |
| MEAN DIFF OF STDS | 0.18 | 0.19 | 0.11 | 0.15 | 0.07 |
| (Std dev) | (0.05) | (0.14) | (0.05) | (0.08) | (0.06) |
| Bstd/Bo | 0.71 | 0.59 | 0.49 | 0.50 | 0.59 |
| False pos 0 ppm | 0 | 0 | 0 | 0 | 0 |
| False pos 0.25 ppm | 0 | 0 | 0 | 0 | 0 |
| False neg 1.0 ppm | 0 | 0 | 1 | 0 | 0 |

Also, the operators ran five field samples at two target levels, 1.0 and 10.0 ppm. The results of these samples correlated with the GC results and the results of the present test kit run by the trained operators.

The results of these experiments clearly indicate the useability of the test and the lack of operator variation.

Lot to lot variability was assessed by comparing the sensitivity profiles generated from three validation lots. All three lots demonstrated a consistent number of false results with the following percent negative results at 0.40 ppm: Lot 1-100%, Lot 2-94% and Lot 3-100%, and at 1.0 ppm: Lot 1-1%, Lot 2-4.1% and Lot 3-6.8%. These experiments indicate that the product is reproducible and not subject to inter-person, day or lot variations.

Sensitivity profiles on spiked or negative soil were used to evaluate the effective temperature range. The accuracy, sensitivity and specificity of the test remained constant over the range of 4°–30° C.

Example 6

The assay test kit of the present invention showed little loss in performance when stored at room temperature (20°–30° C.) for 3 months. Regression analysis evaluating signal decay and performance suggests long-term stability (>6 months) when stored at room temperature.

Therefore, the data suggest that the assay method of the present invention is an acceptable, and more conservative, field screening method for PCB contamination.

The advantages of immunoassay technology can be attributed to the underlying lock and key binding principle and its compatibility with aqueous matrixes. This method does not require the chromatographic separation of sample components, nor does it require that compounds absorb visible, infrared or UV for detection. Interferences from other compounds are considerably less of a problem because of the conformational nature of the antibody binding process. Sample processing time is significantly reduced, and the direct testing of aqueous samples, or water-compatible extracts of soil, can be performed. The technology offers a unique, and conservative, approach to field screening. The incidence of false negative data is exceptionally low. Aspects that tend to interfere with immunoassay methods of this type tend to cause an overestimation of contamination, or false positive result by minimizing the binding of enzyme conjugate to antibody or suppressing signal generation by the enzyme.

This method offers significant versatility and performance advantages. It is a convenient and effective new tool that can enhance the efficiency of site management activities and the utilization of our national laboratory system.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letter Patent of the United States is:

1. A monoclonal antibody useful for detecting the presence of PCB's in a sample, having specific reactivity towards AROCLORs 1260, 1254, 1248, 1242, 1232, 1016 and 1221 that is substantially the same as the monoclonal antibody produced by clone ATCC No. HB-12421.

2. The monoclonal antibody of claim 1, obtained by (i) providing an immune response in a vertebrate host by immunization with an immunogen comprised of a derivative moiety of formula:

$$X_n\text{-}\phi\text{-}Y_m\text{-}\phi\text{-}R_1\text{-}(CH_2)_p\text{-}R_2\text{-}$$

wherein X and Y independently represent a halogen n is an integer from 0 to 5, m is an integer from 0 to 4, wherein n and m cannot both be 0;

$R_1$ is $$-\overset{O}{\overset{\|}{C}}-NH-,\ -NH-\overset{O}{\overset{\|}{C}}-,\ CH_2\overset{O}{\overset{\|}{C}}-NH-,\ -\overset{O}{\overset{\|}{C}}-,\ -\overset{|}{N}R_3$$

or a single bond

R₂ is

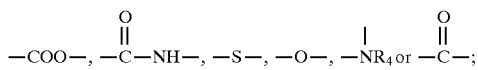

wherein R₃ and R₄ are each independently hydrogen, $C_1$-$C_2$ alkyls, linear, branched, or cyclic $C_3$-$C_6$ alkyls; and p is 0 or an integer from 1 to 4;
linked to an immunogen carrier molecule;
(ii) preparing a hybridoma from the lymphoid cells of said host;
(iii) selecting said hybridoma which produces said monoclonal antibody; and
(iv) obtaining said monoclonal antibody.

3. An immunoassay kit useful for detecting the presence of PCB's in a sample, comprising a monoclonal antibody having specific reactivity towards AROCLORs 1260, 1254, 1248, 1242, 1232, 1016 and 1221 that is substantially the same as the monoclonal antibody produced by clone ATCC No. HB-12421.

4. An immunoassay kit useful for detecting the presence of PCB's in a sample, said kit comprising
(i) a reaction vessel means containing an immobilized monoclonal antibody having specific reactivity towards AROCLORs 1260, 1254, 1248, 1242, 1232, 1016 and 1221 that is substantially the same as the monoclonal antibody produced by clone ATCC No. HB-12421,
(ii) a standard solution comprising at least one of AROCLOR 1260, AROCLOR 1254 or AROCLOR 1248, and a solvent;
(iii) a hapten-reporter moiety-containing reagent which is cross-reactive with said antibody, and a suitable solvent; and
(iv) means for causing said reporter moiety to generate a signal and means for detecting the signal.

5. The kit of claim 5, wherein said hapten-reporter moiety-containing reagent is a compound of formula

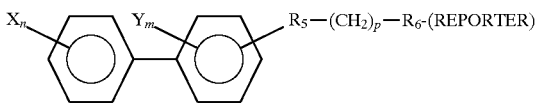

wherein X and Y independently represent a halogen
n is an integer from 0 to 5,
m is an integer from 0 to 4, wherein n and m cannot both be 0;
R₅ is

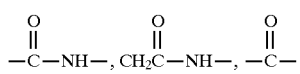

or a single bond
R₆ is

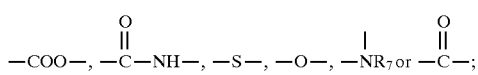

wherein R₇ is hydrogen, $C_1$-$C_2$ alkyls, linear, branched, or cyclic $C_3$-$C_6$ alkyls; and
p is 0 or an integer from 1 to 4; linked to a reporter molecule.

6. The kit of claim 4, wherein said standard solution comprises from 0.6 to 10 ppm of said compound.

7. The kit of claim 5, wherein said reporter molecule is an enzyme selected from the group consisting of horseradish peroxidase, alkaline phosphatase, β-galactosidase, glucose oxidase, G6-PDH and urease.

8. The kit of claim 4, wherein said reaction vessel means is a plurality of vessels, each containing an equivalent amount of said monoclonal antibody.

9. An immunoassay for determining the presence of PCB's in a sample, comprising:
(i) combining (ia) a monoclonal antibody with specific reactivity towards AROCLORs 1260, 1254, 1248, 1242, 1232, 1016 and 1221 that is substantially the same as the monoclonal antibody produced by clone ATCC No. HB-12421, with (ib) a mixture of (ibi) the sample and (ibii) a hapten-and-reporter-molecule reagent which is cross reactive with said monoclonal antibody, wherein said reporter molecule is susceptible to producing a detectable signal, to form an assay mixture;
(ii) incubating said assay mixture to allow competitive monoclonal antibody binding between at least one of said AROCLORs, if present, in the sample, and said reagent;
(iii) causing production of said detectable signal and correlating said signal to the amount of reagent bound to said monoclonal antibody to obtain a measure of the amount of PCB's in said sample.

10. The immunoassay of claim 9, comprising using an immobilized monoclonal antibody.

11. The immunoassay of claim 9, comprising using said hapten-reporter molecule reagent of the formula

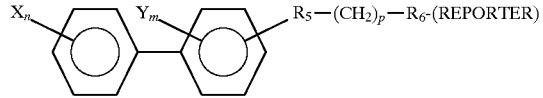

wherein X and Y independently represent a halogen
n is an integer from 0 to 5,
m is an integer from 0 to 4, wherein n and m cannot both be 0;
R₅ is

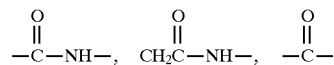

or a single bond
R₆ is

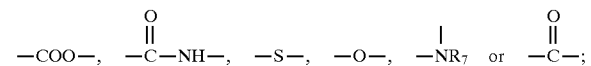

wherein R₇ is hydrogen, $C_1$-$C_2$ alkyls, linear, branched, or cyclic $C_3$-$C_6$ alkyls; and
p is 0 or an integer from 1 to 4;
linked to a reporter molecule.

12. The immunoassay of claim 11, wherein said reporter molecule is an enzyme selected from the group consisting of horseradish peroxidase, alkaline phosphatases, β-galactosidase, glucose oxidase, G6-PDH and urease.

13. The immunoassay of claim 12, wherein said enzyme is horseradish peroxidase.

14. The immunoassay of claim 9, further comprising simultaneously assaying a standard solution of at least one of AROCLOR 1260, AROCLOR 1254 or AROCLOR 1248 and said sample.

15. The kit of claim 4, wherein said kit is a wipe test kit used to detect PCBs on a solid surface and further comprises:
   (a) an extraction vessel having therein an extraction solvent;
   (b) a wiping means; and
   (c) a wiping template.

16. The kit of claim 15, wherein said wiping means is a cloth having dimensions of 4 in by 4 in.

17. The kit of claim 15, wherein said extraction solvent is methanol.

18. The kit of claim 15, wherein said wiping template provides a controlled wiping area of 100 cm$^2$.

19. The kit of claim 4, wherein said kit is an immunoassay kit for testing of soil matrix samples and further comprises:
   (1) a dispersion vessel and dispersing means;
   (2) a dispersion solvent; and
   (2) a filtration means.

20. The kit of claim 19, wherein said dispersing means is one or more conventional dispersing pellets.

21. The kit of claim 19, wherein said dispersion solvent is methanol.

22. The kit of claim 19, wherein said filtration means is a fingertip-operated filter unit fitted with one or more non-adsorbing filters.

23. A monoclonal antibody useful for detecting the presence of PCB's in a sample, wherein said monoclonal antibody is a monoclonal antibody produced by clone ATCC No. HB-12421.

24. An immunoassay kit useful for detecting the presence of PCB's in a sample, comprising a monoclonal antibody produced by clone ATCC No. HB-12421.

25. An immunoassay kit useful for detecting the presence of PCB's in a sample, said kit comprising
   (i) a reaction vessel means containing an immobilized monoclonal antibody wherein the immobilized monoclonal antibody is a monoclonal antibody produced by clone ATCC No. HB-12421,
   (ii) a standard solution comprising at least one of AROCLOR 1260, AROCLOR 1254 or AROCLOR 1248, and a solvent;
   (iii) a hapten-reporter moiety-containing reagent which is cross-reactive with said antibody, and a suitable solvent; and
   (iv) means for causing said reporter moiety to generate a signal and means for detecting the signal.

26. An immunoassay for determining the presence of PCB's in a sample, comprising:
   (i) combining (ia) a monoclonal antibody produced by clone ATCC No. HB-12421, with (ib) a mixture of (ibi) the sample and (ibii) a hapten-and-reporter-molecule reagent which is cross reactive with said monoclonal antibody, wherein said reporter molecule is susceptible to producing a detectable signal, to form an assay mixture;
   (ii) incubating said assay mixture to allow competitive monoclonal antibody binding between at least one of said AROCLORs, if present, in the sample, and said reagent;
   (iii) causing production of said detectable signal and correlating said signal to the amount of reagent bound to said monoclonal antibody to obtain a measure of the amount of PCB's in said sample.

* * * * *